(12) United States Patent
Ross, Jr. et al.

(10) Patent No.: US 9,282,897 B2
(45) Date of Patent: Mar. 15, 2016

(54) BELT-MOUNTED MOVEMENT SENSOR SYSTEM

(75) Inventors: Johnny Ross, Jr., Mansfield, TX (US); Jagdeepinder Singh Sanghera, Midlothian, TX (US)

(73) Assignee: Medhab, LLC, Mansfield, TX (US)

( * ) Notice: Subject to any disclaimer, the term of this patent is extended or adjusted under 35 U.S.C. 154(b) by 1068 days.

(21) Appl. No.: 13/371,658

(22) Filed: Feb. 13, 2012

(65) Prior Publication Data
US 2013/0211772 A1  Aug. 15, 2013

(51) Int. Cl.
*A61B 5/11* (2006.01)
*A61B 5/00* (2006.01)

(52) U.S. Cl.
CPC ............ *A61B 5/0022* (2013.01); *A61B 5/1118* (2013.01); *A61B 5/6823* (2013.01); *A61B 5/6831* (2013.01); *A61B 5/6841* (2013.01); *A61B 2562/0219* (2013.01); *A61B 2562/046* (2013.01)

(58) Field of Classification Search
USPC ............... 702/130, 131, 142, 141; 340/573.1; 601/34; 607/62; 600/459
See application file for complete search history.

(56) References Cited

U.S. PATENT DOCUMENTS

| | | | |
|---|---|---|---|
| 4,757,453 A | 7/1988 | Nasiff | |
| 4,830,021 A | 5/1989 | Thornton | |
| 4,846,181 A | 7/1989 | Miller | |
| 5,125,412 A | 6/1992 | Thornton | |
| 5,980,472 A | 11/1999 | Seyl | |
| 6,032,530 A | 3/2000 | Hock | |
| 6,059,576 A | 5/2000 | Brann | |
| 6,148,280 A | 11/2000 | Kramer | |
| 6,165,143 A | 12/2000 | Van Lummel | |
| 6,416,471 B1 | 7/2002 | Kumar | |
| 6,840,955 B2 | 1/2005 | Ein | |
| 6,881,191 B2 | 4/2005 | Oakley et al. | |
| 6,984,208 B2 | 1/2006 | Zheng | |
| 7,192,387 B2 | 3/2007 | Mendel | |
| 7,210,240 B2 | 5/2007 | Townsend | |
| 7,313,440 B2 | 12/2007 | Miesel | |
| 7,365,647 B2 | 4/2008 | Nativ | |
| 7,373,820 B1 | 5/2008 | James | |
| 7,387,611 B2 | 6/2008 | Inoue | |
| 7,503,878 B1 | 3/2009 | Amsbury | |
| 7,602,301 B1 * | 10/2009 | Stirling et al. | ............. 340/573.1 |
| 7,625,316 B1 | 12/2009 | Amsbury | |
| 7,634,379 B2 | 12/2009 | Noble | |

(Continued)

FOREIGN PATENT DOCUMENTS

| | | |
|---|---|---|
| JP | 2004141669 A | 5/2001 |
| JP | 2009125508 A | 6/2009 |

(Continued)

*Primary Examiner* — Mohamed Charioui
(74) *Attorney, Agent, or Firm* — Eric Karich; Karich & Associates

(57) ABSTRACT

A belt-mounted movement sensor system apparatus has a flexible belt shaped to be worn around the midsection of the user. The system has an array of accelerometers disposed on or within the flexible belt to physically associate with positions on the midsection of the user. Each array of accelerometers has a sample rate that can be configured for sensing body movement during a movement activity. A power source and a data collection system are operably connected to the array of accelerometers. The data collection system has a means for receiving data from the array of accelerometers and processing that data into a storable format.

2 Claims, 6 Drawing Sheets

(56) References Cited

U.S. PATENT DOCUMENTS

| | | |
|---|---|---|
| 7,640,804 B2 | 1/2010 | Daumer et al. |
| 7,658,695 B1 | 2/2010 | Amsbury et al. |
| 7,712,365 B1 | 5/2010 | James |
| 7,825,815 B2 | 11/2010 | Shears |
| 7,843,351 B2 | 11/2010 | Bourne |
| 2003/0054923 A1 | 3/2003 | Brassil et al. |
| 2003/0126593 A1 | 7/2003 | Mault |
| 2003/0139692 A1 | 7/2003 | Barrey et al. |
| 2003/0199945 A1 | 10/2003 | Ciulla |
| 2004/0159109 A1* | 8/2004 | Harvie ............... 62/3.5 |
| 2006/0122528 A1 | 6/2006 | Gal |
| 2007/0032748 A1 | 2/2007 | McNeil et al. |
| 2007/0112286 A1 | 5/2007 | Prichard |
| 2007/0285868 A1 | 12/2007 | Lindburg et al. |
| 2008/0009926 A1 | 1/2008 | Russak et al. |
| 2008/0015457 A1 | 1/2008 | Silva |
| 2008/0108918 A1* | 5/2008 | Joutras et al. .......... 601/34 |
| 2008/0214360 A1 | 9/2008 | Stirling et al. |
| 2008/0218310 A1 | 9/2008 | Alten et al. |
| 2008/0319277 A1 | 12/2008 | Bradley |
| 2009/0062092 A1 | 3/2009 | Mortimer |
| 2009/0069642 A1 | 3/2009 | Gao et al. |
| 2009/0112098 A1 | 4/2009 | Vaezy et al. |
| 2009/0318779 A1 | 12/2009 | Tran |
| 2010/0088803 A1 | 4/2010 | Orloff |
| 2010/0117837 A1 | 5/2010 | Stirling et al. |
| 2010/0152621 A1 | 6/2010 | Janna et al. |
| 2010/0152623 A1 | 6/2010 | Williams |
| 2010/0204616 A1 | 8/2010 | Shears et al. |
| 2010/0286571 A1 | 11/2010 | Allum et al. |
| 2010/0312297 A1 | 12/2010 | Volpe et al. |
| 2011/0013713 A1 | 1/2011 | Li et al. |
| 2011/0066041 A1 | 3/2011 | Pandia et al. |
| 2011/0077526 A1* | 3/2011 | Zwirn ................. 600/459 |
| 2012/0016446 A1* | 1/2012 | Panting ................ 607/62 |

FOREIGN PATENT DOCUMENTS

| | | |
|---|---|---|
| JP | 2010507398 | 3/2010 |
| WO | WO 0110508 | 2/2001 |
| WO | WO2009/080419 | 7/2009 |
| WO | WO2009112281 | 9/2009 |
| WO | WO2010/077851 | 7/2010 |
| WO | WO2010/082827 | 7/2010 |
| WO | WO 2010/089828 | 8/2010 |

\* cited by examiner

BELT-MOUNTED MOVEMENT SENSOR SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates generally to therapeutic devices, and more particularly to a belt-mounted movement sensor system for assisting a patient with physical rehabilitation of a back injury.

2. Description of Related Art

The prior art teaches various forms of monitoring systems and therapeutic devices for monitoring a patient.

Mault, U.S. publication 2003/0126593, teaches a physiological monitoring system that has a monitor module, which monitors a physiological parameter of the person, the module having a wireless transmitter such as a Bluetooth transmitter. The system further comprises an interactive television system, which receives a signal from a remote control unit, such as an IR or other wireless transmission, wherein the received signal is used to modify visual presentations on a display of the interactive television system, such as changing a channel, providing numerical data in response to presented menus, selecting from presented menus using navigation keys, and the like. The system further includes a portable computing device, adapted to receive physiological data transmitted by the monitor module and to store the physiological data in a memory, and which is further adapted to function as the remote control unit of the interactive TV, so as to transmit stored physiological data to the digital interactive television, and to provide a signal for remote control and interaction with the interactive TV.

James, U.S. Pat. No. 7,712,365, teaches a monitoring device that includes an accelerometer for monitoring a mammal. The monitoring device includes a computer reporting device that receives data about the movements of the mammal, and reports activity in response to certain predetermined conditions.

Shears et al., U.S. 2010/0204616, teaches a system for measuring and analyzing movements of a body, and for communicating information about the body movements over a network. The system gathers biometric and biomechanical data related to positions, orientations, and movements of body parts during sports activities, physical rehabilitation, and military/law enforcement activities. The system includes a controller operably connected with a plurality of sensors. The sensors are attached to the user at strategic locations of the user's body (e.g., with an adhesive) to monitor movement of the user during, for example, a golf swing.

The above-described references are hereby incorporated by reference in full.

SUMMARY OF THE INVENTION

The present invention teaches certain benefits in construction and use which give rise to the objectives described below.

The present invention provides a belt-mounted movement sensor system for tracking and recording movement data of a midsection of a user. The belt-mounted movement sensor system includes a flexible belt shaped to abut the midsection of the user and is adapted to be worn around the midsection of the user. The system has an array of accelerometers disposed on or within the planar body of the flexible belt to physically associate with positions on the midsection of the user. Each array of accelerometers has a sample rate that can be configured for sensing body movement during a movement activity. A power source and a data collection system are operably connected to the array of accelerometers. The data collection system has a means for receiving data from the array of accelerometers and processing that data into a storable format.

A primary objective of the present invention is to provide a belt-mounted movement sensor system having advantages not taught by the prior art.

Another objective is to provide a belt-mounted movement sensor system that can collect movement data and transmit this information to a computer device, to be stored and analyzed.

A further objective is to provide a belt-mounted movement sensor system that collects detailed information about the particular orientation and movement of many strategic points of the user's midsection, to more accurately track the user's movements to ensure activities, such as physical rehabilitation, are performed correctly.

A further objective is to provide a belt-mounted movement sensor system that has the capability to heat and cool the user's midsection, as deemed therapeutically appropriate by a clinician.

A further objective is to provide a belt-mounted movement sensor system that contains both a power supply and a data collection system to reduce the amount of separate devices required to measure and analyze the user's movement.

A further objective is to provide a belt-mounted movement sensor system that can be readily adjusted for operation with users of different sizes.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, a belt-mounted movement sensor system 10 for tracking and recording movement data of a midsection 14 of a user 12.

Figure 1:
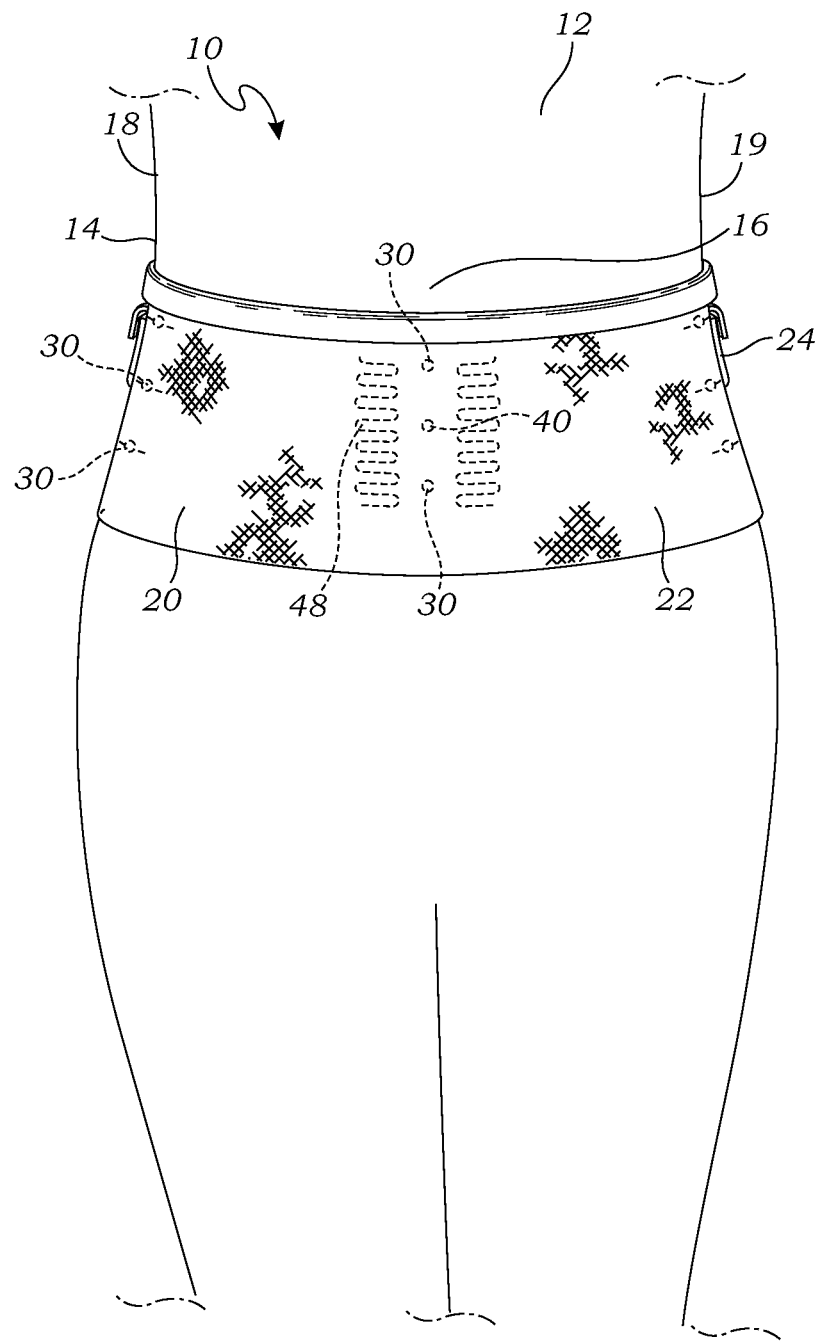
FIG. 1 is a rear perspective view of a user wearing one embodiment of a belt-mounted movement sensor system.
Figures 2, 3:
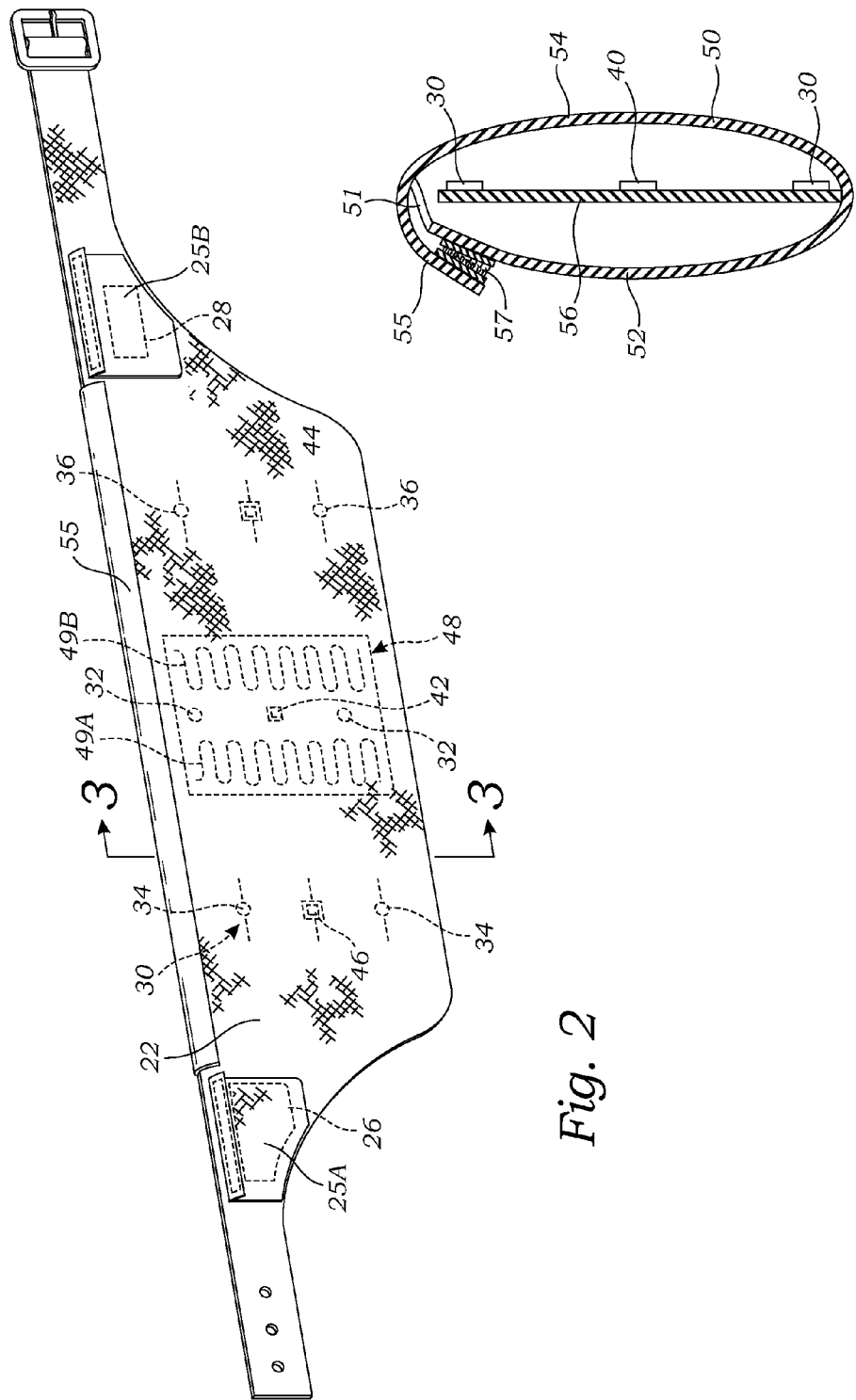
FIG. 2 is a top plan view of the belt-mounted movement sensor system in an open configuration when not being worn by the user.
FIG. 3 is a sectional view thereof taken along line 3-3 in FIG. 2.

FIG. 1 is a rear perspective view of the user 12 wearing one embodiment of the belt-mounted movement sensor system 10. FIG. 2 is a top plan view of the belt-mounted movement sensor system 10 in an open configuration when not being worn by the user 12, to better illustrate the construction of the belt-mounted movement sensor system 10. As shown in FIGS. 1 and 2, the belt-mounted movement sensor system 10 includes a flexible belt 20, an array of accelerometers 30, a power source 26, and a data collection system 28.

As illustrated in FIGS. 1 and 2, the flexible belt 20 is adapted to be worn around the midsection 14 of the user 12 to monitor the user's movement. The flexible belt 20 has a planar body 22 shaped to abut the midsection 14 of the user 12 and has at least one storage compartment 24. In the present embodiment, the flexible belt 20 includes a first storage compartment 25A shaped to contain the power source 26, and a second storage compartment 25B shaped to contain the data collection system 28, which, in this case, is a data collector that is a separate piece of electronics illustrated further in FIG. 6. However, in alternative embodiments, both the power source 26 and the data collection system 28 may be mounted in a single compartment. The term "compartment" is hereby defined to broadly include any form of compartment, recess, or other mounting feature suitable for mounting the power source 26 and the data collection system 28 on the flexible belt 20.

Furthermore, in another embodiment (not illustrated), the power source 26 and the data collection system 28 may also be provided as a single unit (i.e., the power source may be integrated with the data collection system). In yet another embodiment, illustrated in FIG. 7, the data collection system is provided elsewhere in a computer network described in greater detail below. While one embodiment of the flexible belt 20 is illustrated, the particular shape and form of the belt may vary according to the design of one skilled in the art.

The array of accelerometers 30 is disposed on or within the planar body 22 of the flexible belt 20 to physically associate with positions on the midsection 14 of the user 12. Each array of accelerometers 30 has a sample rate that can be configured for sensing body movement during a movement activity. The power source 26 is stored in the at least one storage compartment 24 of the flexible belt 20 and is operably connected to the array of accelerometers 30. The data collection system 28 is also adapted to be stored in the at least one storage compartment 24 of the flexible belt 20 and is operably connected to the array of accelerometers 30. The data collection system 28 has a means for receiving data from the array of accelerometers 30 and processing that data into a storable format.

The belt-mounted movement sensor system 10 may further include at least one gyroscope 40 operably mounted on the flexible belt 20 adjacent to the array of accelerometers 30 for measuring an orientation of the flexible belt 20 while being worn by the user 12. Both the accelerometers and the gyroscope(s) are well known in the art, and any suitable embodiments of these may be utilized, according to one skilled in the art.

In the embodiment of FIG. 1-2, the array of accelerometers 30 may include at least two central accelerometers 32 that are mounted in a line on the flexible belt 20 in a manner that allows them to align with the spine 16 of the user 12 when the flexible belt 20 is worn. The array of accelerometers 30 may further include at least two left-side accelerometers 34 that are mounted in a line on the flexible belt 20 in a manner that allows them to align with the left side 18 of the user 12 when the flexible belt 20 is worn, and further includes at least two right-side accelerometers 36 that are mounted in a line on the flexible belt 20 in a manner that allows them to align with the right side 19 of the user 12 when the flexible belt 20 is worn.

In this embodiment, the at least one gyroscope 40 includes a central gyroscope 42 that is operably mounted on the flexible belt 20 between each of the two central accelerometers. Furthermore, a right-side gyroscope 44 and a left-side gyroscope 46, depicted in FIG. 1-2, may be included. In this embodiment, the right-side gyroscope 44 is operably mounted on the flexible belt 20 between two right-side accelerometers 36, and the left-side gyroscope 46 is operably mounted on the flexible belt 20 between two left-side accelerometers 34.

While FIGS. 1 and 2 illustrate one embodiment of the array of accelerometers 30 and the at least one gyroscope 40, other arrangements of the accelerometers and the gyroscopes may also be utilized. Alternative arrangements that may be selected by one skilled in the art are also considered within the scope of the present invention.

In the embodiment of FIG. 1-2, heating coils 48 are operably mounted on the flexible belt 20 to apply heat to the midsection 14 of the user 12 while he or she is wearing the belt. Using this embodiment of the flexible belt 20 enables the user 12 to move and/or perform rehabilitation exercises while being monitored and also while being heated by the heating coils 48, which help the user 12 avoid injury. In the present embodiment, the heating coils 48 include a left coil 49A and a right coil 49B positioned on both sides of the two central accelerometers 32. The heating coils 48 may be used to alleviate back pain, reduce inflammation, or achieve other therapeutic goals known within the field. The term "heating coil" is hereby defined to include any form of heating element that is known to those skilled in the art to apply therapeutic heat to the user 12 wearing this form of belt-like device, and the term should be broadly construed. While one embodiment of the heating coils 48 is illustrated, other arrangements of heating coils or equivalent elements may also be utilized, and should be considered within the scope of the present invention.

FIG. 3 is a sectional view of the flexible belt 20 taken along line 3-3 in FIG. 2. As illustrated in FIG. 3, the flexible belt 20 may include an outer shell 50 and an inner sensor sheet 56 positioned within the outer shell 50. The outer shell 50 may include an outer portion 52, as well as an inner portion 54 that is adapted to abut the user 12 (as illustrated in FIG. 1). The array of accelerometers 30 may be operably mounted on the inner sensor sheet 56, which is shaped to be positioned within the outer shell 50 between the inner portion 54 and the outer portion 52. The outer shell 50 may be, for example, a flexible fabric or similar material that may be padded, and that is preferably washable and/or disposable. The inner portion 54 is adapted to abut the user 12, so that it should be comfortable to wear. The outer portion 52 may be constructed of the same material as the inner portion 54, or it may be a more durable material to protect the inner sensor sheet 56.

In the embodiment of FIG. 3, the outer shell 50 includes an opening 51 for inserting the inner sensor sheet 56 into the outer shell 50. The opening 57 may include a flap 55 having a fastener 57 (e.g., hook-and-loop fasteners, or any similar fastener known in the art) for closing the inner sensor sheet 56 within the outer shell 50. In this manner, the inner sensor sheet 56 is protected during use, but may be removed for cleaning/replacing the outer shell 50.

Figure 4:
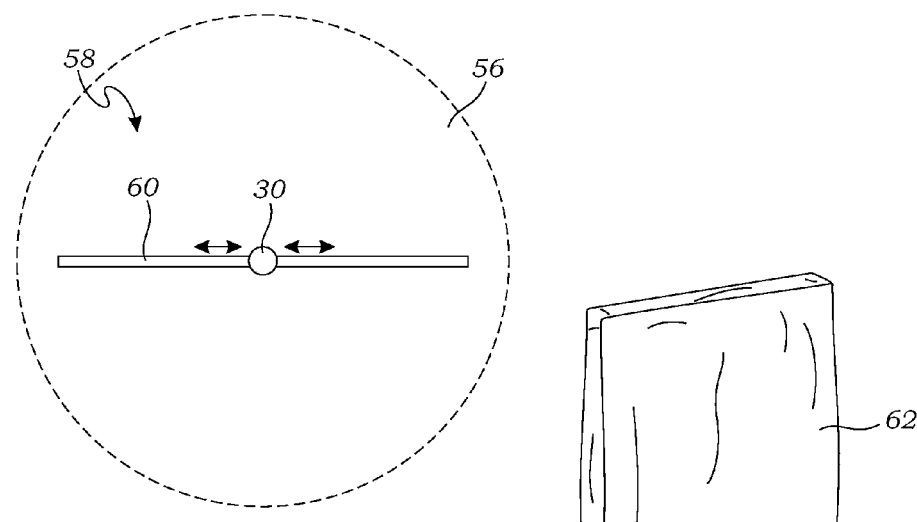
FIG. 4 is a close up view of an accelerometer of FIG. 2 mounted on an adjustment track for lateral adjustment of the position of the accelerometer.

FIG. 4 is a close up view of one of the array of accelerometers 30 of FIG. 2 mounted on an adjustment track 58 for lateral adjustment of the position of the accelerometer. The term "adjustment track" is hereby defined to include any equivalent mechanism for adjusting the lateral position of some of the accelerometers. In the embodiment of FIG. 4, the adjustment track 58 includes lateral slots 60, wherein each of the at least two left-side accelerometers 34 and each of the at least two right-side accelerometers 36 are operably mounted on one of the lateral slots 60 of the flexible belt 20, so that they each may be adjusted laterally to coincide with the side of the user 12.

The adjustment tracks 58 enable the adjustment of the array of accelerometers 30 so that they are correctly positioned with respect to the user 12. While one embodiment of the adjustment track 58 is illustrated, alternative embodiments of the adjustment track 58, which may be devised by one skilled in the art, should be considered within the scope of the present invention.

Figure 5:
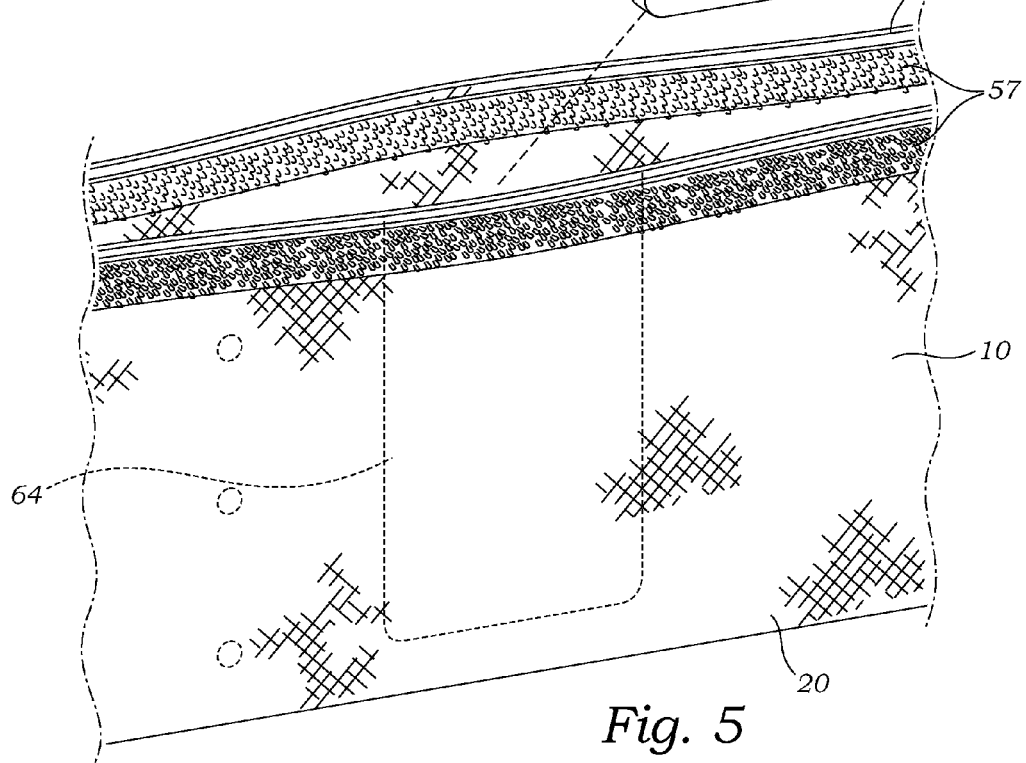
FIG. 5 is an exploded perspective view of the belt-mounted movement sensor system, illustrating a cold pack being positioned in a pocket of the belt-mounted movement sensor system.

FIG. 5 is an exploded perspective view of the belt-mounted movement sensor system 10, illustrating a cold pack 62 being positioned in a compartment 64 of the flexible belt 20. The cold pack 62 may be utilized to alleviate back pain, reduce inflammation, or achieve other therapeutic aims of those skilled in the art. The term "compartment" is hereby defined to broadly include any form of compartment, recess, or other mounting feature suitable for mounting the cold pack 62 on the flexible belt 20. In alternative embodiments, however, the cold pack 62 may be positioned in other locations and may be enclosed in the flexible belt 20 with metal snaps, zippers, or alternative means of fastening.

Figure 6:
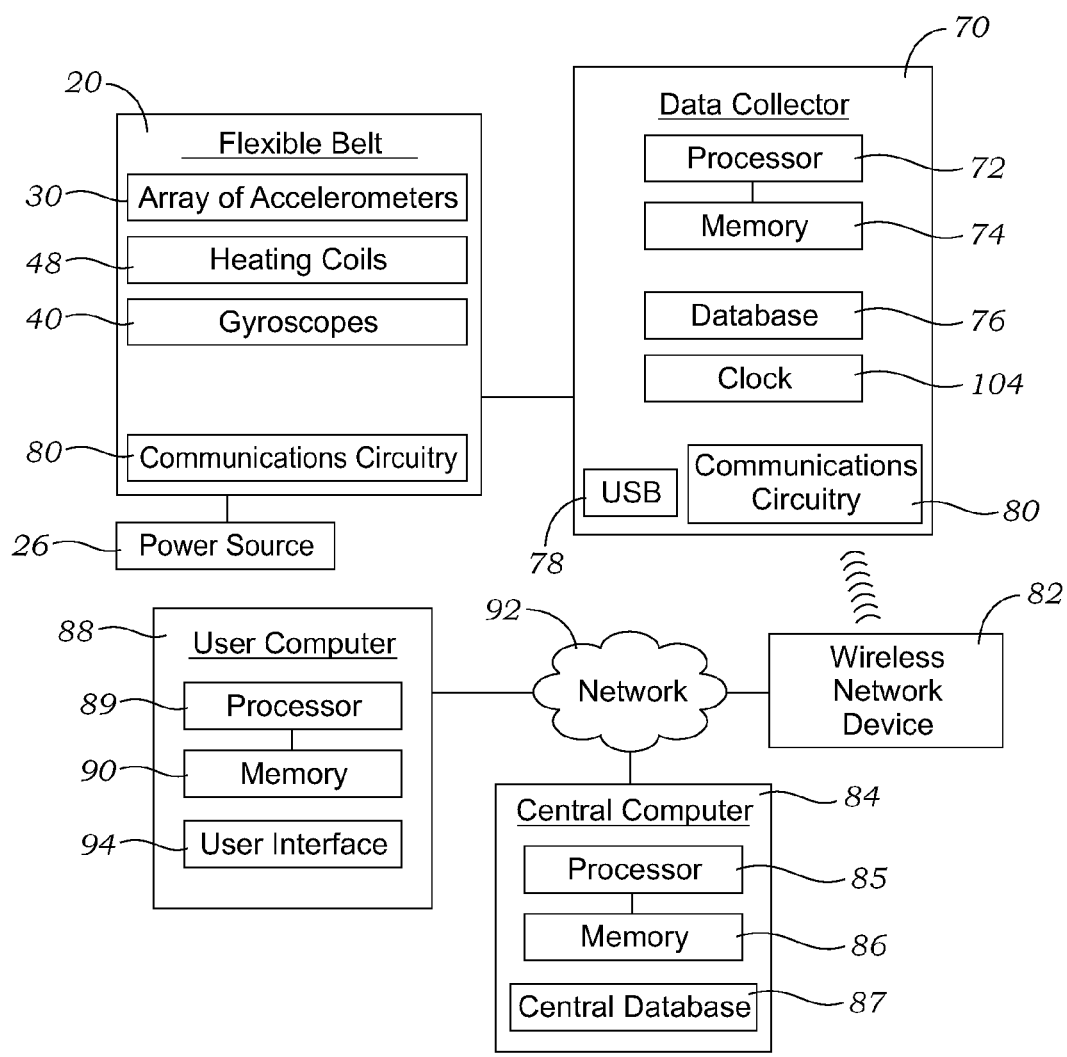
FIG. 6 is a block diagram of the belt-mounted movement sensor system of FIG. 1.

FIG. 6 is a block diagram of the belt-mounted movement sensor system 10. In this embodiment, the belt-mounted movement sensor system 10 includes a data collection system 70 for receiving data from the array of accelerometers 30. The array of accelerometers 30 may be used to convert acceleration into an electrical signal. Therefore, the array of accelerometers 30 may receive input and provide digital output that reflects this activity, which may then be collected, transmitted, stored (e.g., to a computer), and analyzed. The user 12 may be any individual whose movement requires close tracking, such as a medical patient in rehabilitation, an athlete (in training, therapy, etc.), or other person, such as an employee or person working in a remote environment. Those skilled in the art may devise a wide range of uses of this system 10, and such alternatives should be considered within the scope of the present invention.

The data collection system 70 of FIG. 6 includes a controller that includes a processor 72 and a memory 74. The controller may be used for maintaining a database 76, and/or operably controlling functions of the system 10, as discussed in greater detail below. Furthermore, while one embodiment of the controller is described herein, alternative embodiments may also be used; for example, a computer separate from the belt may be utilized, which is discussed at length below.

The processor 72 and the memory 74 may be configured to receive data from the array of accelerometers 30 and process that data into a storable format. The data collection system 70 may also include a USB port 78 (or any other suitable connection) for operably connecting the data collection system 70 with a computer, such as a central computer 84 as illustrated. Additionally, the data collection system 70 may also have a communications circuitry 80, which serves to transmit information from the array of accelerometers 30 to a wireless network device 82 to be accessed by the central computer 84 (or any other computer device desired, such as a user computer 88). The data collection system 70 may further include a clock 104 to enable the system to track movement as a function of time, and to determine when certain actions should be taken, when certain therapies should be applied, and for how long they should continue. The construction and function of the clock 104 are well known in the art, and are therefore not discussed in greater detail herein.

FIG. 6 illustrates the central computer 84 and the user computer 88, in which the central computer 84 may have a processor 85 and a memory 86. The processor 85 and the memory 86 may be configured to receive data (e.g., body movement data) transmitted to the data collection system 70 from the array of accelerometers 30 and may process that data into a storable format in a central database 87, to allow for later retrieval and analysis of the data.

The user computer 88 may also have a processor 89 and memory 90, as well as a user interface 94 to allow for data analysis. The central computer 84 and the user computer 88 may be linked to the data collection system 70 by a common network 92 via a wireless network device 82.

The user computer 88 and/or the central computer 84 depicted in FIG. 6 may include a user 12 interface adapted to enable analysis of the body movement data. Thus, the information on these computers may be accessed by any suitable individual (e.g. doctor, physical therapist, employer, etc) who seeks to analyze the collected data. Furthermore, the user computer 88 and/or the central computer 84 may be in a variety of forms, such as a cellular telephone, a laptop computer, a personal computer, a personal digital assistant (PDA), or any other suitable device known in the art. Therefore, while FIG. 6 illustrates one embodiment of the data collection system 70, other arrangements of computers or computer devices may also be utilized.

The user computer 88 is intended to include, generally, a wide range of computing devices used by a wide range of potential data users. Potential persons who may monitor the data include a patient performing physical rehabilitation (checking his or her own progress), a physical trainer overseeing the physical rehabilitation, a physician monitoring the patient's treatment, and also potentially electronic monitors that take electronic action in response to the data. For example, if the movement data suggests errors in the physical rehabilitation exercises, an electronic monitor (e.g., a program on a computer or similar electronic device) might alert the patient and/or his trainer and/or physician, and/or it might take other action, such as emailing the patient a video showing him or her how to perform the exercise more correctly, and/or reminding him or her to do the exercises (if they are not being performed on the correct schedule). The term "user computer" is intended to encompass all of these options, and include any form of monitoring that may be desired by one skilled in the art.

Figure 7:
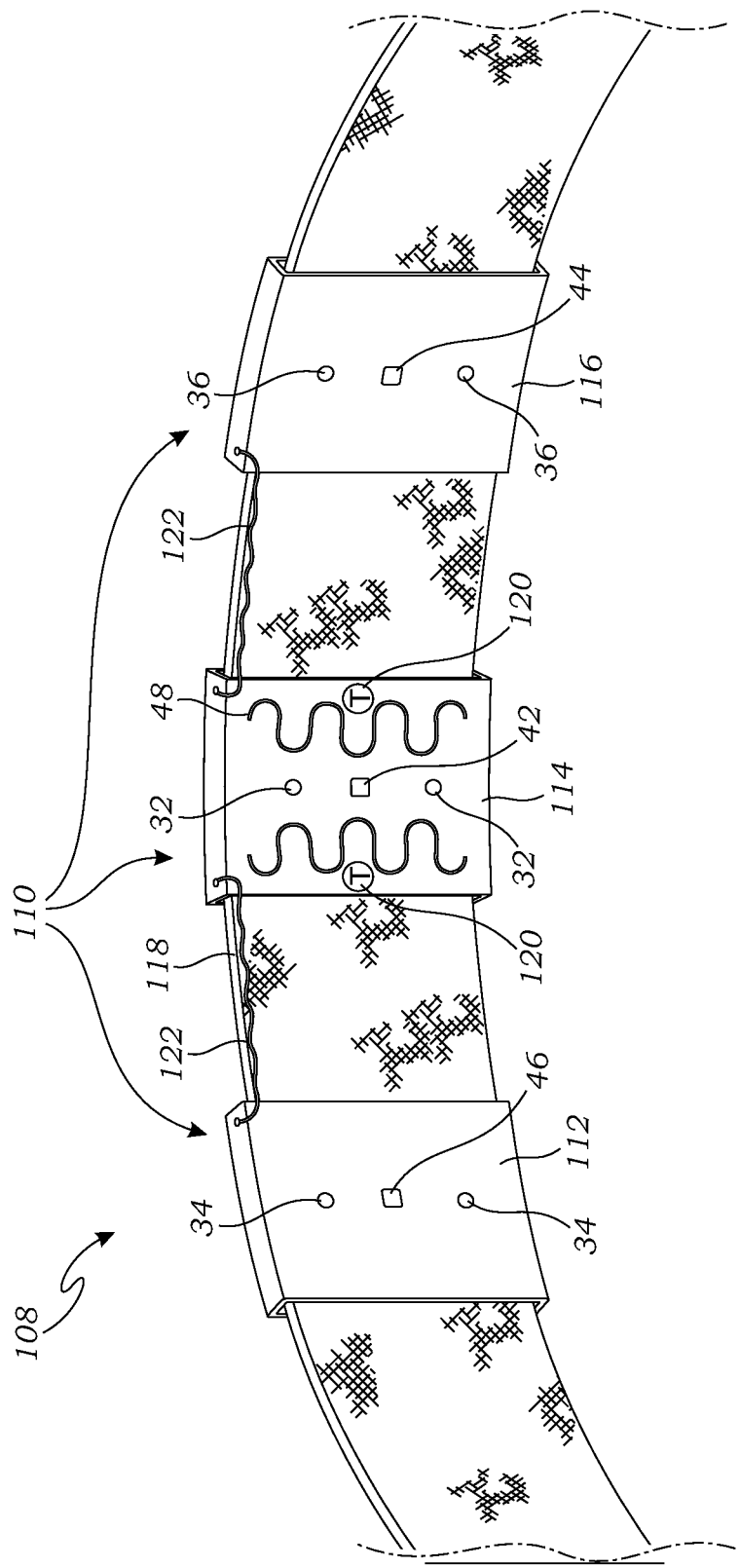
FIG. 7 is a perspective view of a second embodiment of the belt-mounted movement sensor system, illustrating sensor mounting sleeves mounted on an inner belt.

FIG. 7 is a perspective view of a second embodiment of the belt-mounted movement sensor system 108, illustrating sensor mounting sleeves 110 mounted on an inner belt 118. In this embodiment, the inner belt 118 may be inserted through the sensor mounting sleeves 110 so that the sleeves 110 may slide with respect to the inner belt 118, thereby enabling the adjustment of the sleeves 110 with respect to the user. It is not required that all of the sleeves 110 be adjustably mounted, and some of these elements may be fixedly mounted on the inner belt 118 or some other part of the system 108; however, in one embodiment, at least some of the sleeves 110 are adjustable.

In one embodiment, the adjustable sleeves 110 include a left-side sleeve 112, a center sleeve 114, and a right-side sleeve 116. The left and right side sleeves 112 and 116 may be operably attached to the center sleeve 114 with electronic wires 122 (or an equivalent connection). In this embodiment, the left-side sleeve 112 may include at least two left-side accelerometers 34 and a left-side gyroscope 46, and the right-side sleeve may include at least two right-side accelerometers 36 and a right-side gyroscope 44, as discussed above (although other arrangements may also be devised by those skilled in the art). Likewise, the center sleeve 114 of the belt-mounted movement sensor system 10 may include at least two central accelerometers 32, a central gyroscope 42, and heating coils 48, as previously illustrated in FIG. 1-2.

In addition to these elements, the center sleeve 114 may also include temperature sensors 120 to sense temperature in order to maintain a temperature within a range that is desirable to the user 12, to maintain an optimal temperature and to prevent the system 108 from burning the user 12. Although the temperature sensors 120 are depicted on the center sleeve 114 of FIG. 7, alternative locations of the temperature sensors 120 determined by one skilled in the art are considered within the scope of this patent, especially dependent upon the location of the heating coils and other heating/cooling elements.

In the present embodiment of FIG. 7, the sensor mounting sleeves 110 may slide across the inner belt 118 to adjust the location of the array of accelerometers 30, at least one gyroscope 40, heating coils 48, and temperature sensors 120.

Figure 8:
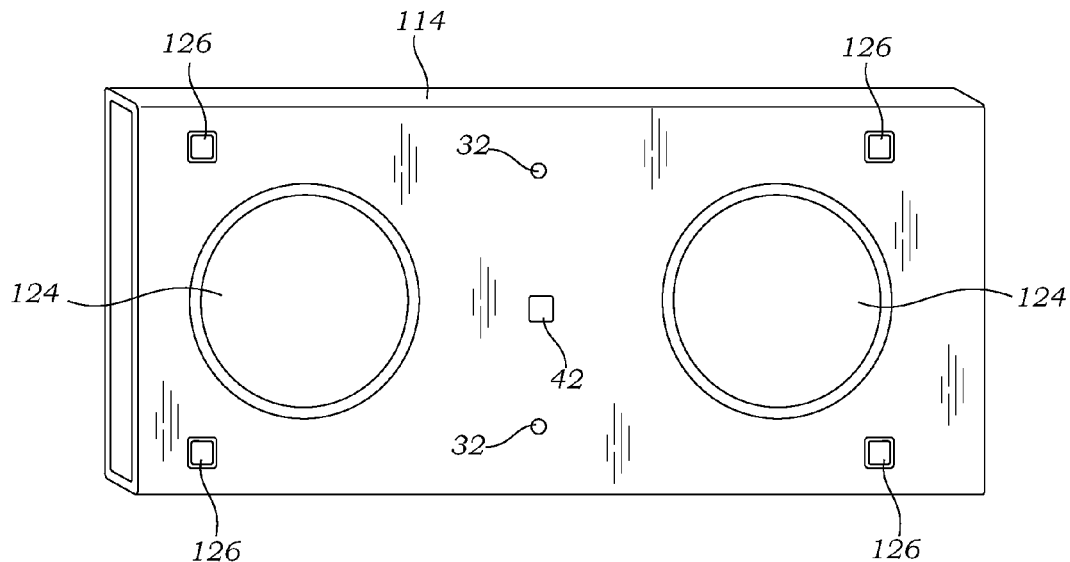
FIG. 8 is a front perspective view of a center sleeve of the sensor sleeves of FIG. 7, illustrating therapeutic ultrasound transducers and electric stimulation contacts of this embodiment.

FIG. 8 is a front perspective view of the center sleeve 114 of FIG. 7, illustrating optional therapeutic ultrasound transducers 124 and electric stimulation contacts 126 of this embodiment. The therapeutic ultrasound transducers 124 may be integrated into the center sleeve 114 (or optionally elsewhere) to provide physical therapy on the user's midsection 14. The term "therapeutic ultrasound transducers" is hereby defined to broadly include any form of device for directing ultrasonic or equivalent waves into the soft tissue of the user. In the present embodiment, the therapeutic ultrasound transducers 124 may emit alternating compression and rarefaction of sound waves into the user's soft tissues, to be absorbed primarily by ligaments, tendons, scar tissue, and fasciae. Thus, the therapeutic ultrasound transducers 124 may benefit the user 12 via thermal effects due to the absorption of the sound waves, as well as non-thermal effects from cavitation. Cavitational effects result from the vibration of the user's tissue, which causes microscopic air bubbles to form and stimulate cell membranes to enhance cell-repair effects of the inflammatory response. Thus, the therapeutic ultrasound transducers 124, coupled with the heating coils 48 and/or cold pack 62, may provide a mobile and effective means to repair injuries to the user 12.

The electric stimulation contacts 126 of FIG. 8 may be included on the center sleeve 114 (or other location) to promote wound healing by utilizing pulsed electrical stimulation. The term "electric stimulation contacts" is hereby broadly defined to include any form of electrical contact for providing electrotherapy in which electrical stimulation is utilized to treat an injury.

In the present form of electrical stimulation therapy, the user 12 undergoes repeated short treatments of electrical stimulation applied to the soft tissue of his or her midsection 14. This electrical stimulation may be capable of delivering pulses at a predetermined pulse intensity and rate so as to treat the user 12 according to a range deemed appropriate by a physician. The electrical stimulation may be provided in conjunction with or in coordination with the rehabilitation exercises monitored by the system 108.

For example, a doctor or other person suitably skilled in the art may devise a treatment plan that includes certain exercises to be performed a certain number of times per day. The treatment may include therapeutic ultrasonic treatment and/or pulsed electrical stimulation before, during, or after each routine, according to a schedule devised by one skilled in the art. These therapies may be provided automatically by this system 108. When the system 108 recognizes, via the accelerometers and/or gyroscopes and/or equivalent sensor, that the user is performing the exercises, it could automatically trigger coordinated ultrasonic therapy to coincide with the exercises. Then, once the exercises have stopped (or after a predetermined period), the system 108 could then also initiate a routine of pulsed electrical stimulation. Such treatment regimes would be devised by skilled persons in the art, such as doctors, but they are enabled using the unique system 108 of the present invention.

It is important to note that both the therapeutic ultrasound transducers 124 and the electric stimulation contacts 126 of FIG. 8 may vary in form and placement according to one skilled in the field. For example, the belt-mounted sensor system 10 may or may not include both the therapeutic ultrasound transducer 124 and the electric stimulation contacts 126, and/or the location of said elements may vary along the flexible belt 20. Alternative embodiments of the ultrasound transducer 124 and the electric stimulation contacts 126 are therefore considered within the scope of the present invention. Furthermore, while the therapeutic ultrasound transducer 124 and the electric stimulation contacts 126 are illustrated as being a part of the second embodiment in FIGS. 7-8, they may also be included in the first embodiment illustrated in FIGS. 1-2.

Figure 9:
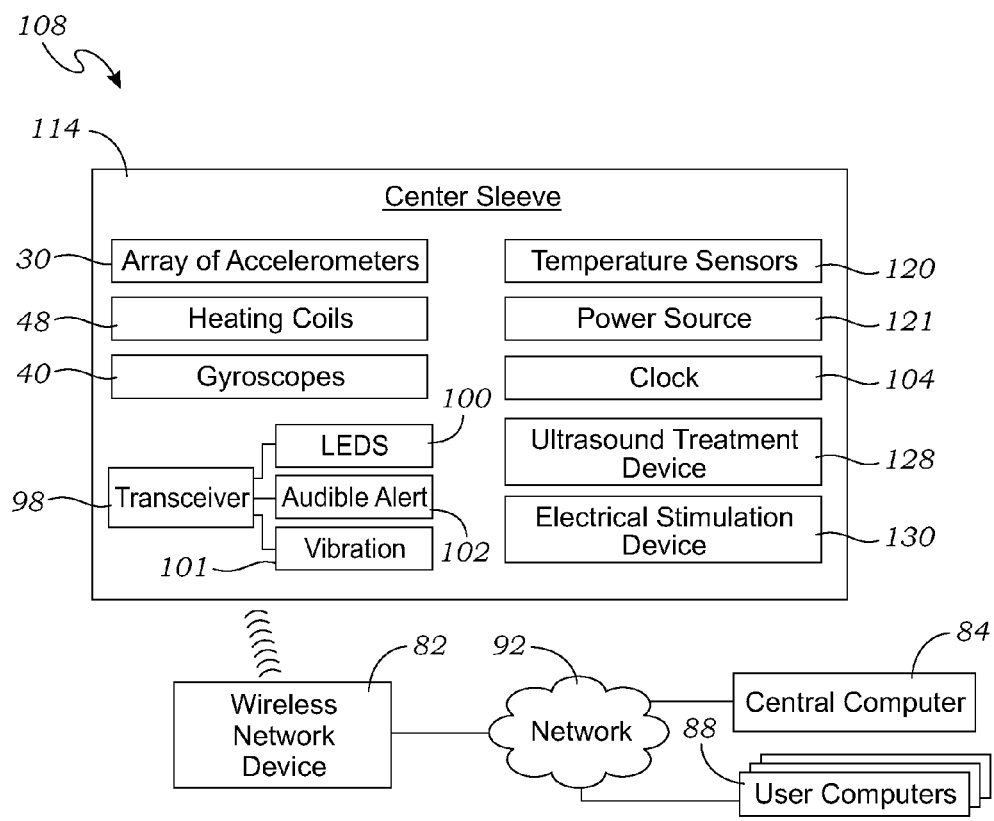
FIG. 9 is a block diagram of one embodiment of the center sleeve of FIG. 7-8.

FIG. 9 is a block diagram of one embodiment of the center sleeve 114 of FIG. 7-8. In this embodiment, the system 108 includes a transceiver 98 operably connected with the array of accelerometers 30 for transmitting body movement data received from the array of accelerometers 30 to a central computer 84 (or some equivalent computer or electronics device). The term "transceiver" is hereby defined to include any device that is known to those skilled in the art for transmitting the data to an outside receiver, and the term should be broadly construed.

In the embodiment of FIG. 7, the transceiver 98 is operably mounted on or within the central sleeve 114, and a data collector device, illustrated above, is not required, and the data is collected and stored at a central computer 84. However, while one embodiment of the data collection system 70 is illustrated, alternative embodiments of the data collection system 70, which may be developed by one skilled in the art, should be considered within the scope of the present invention.

In this embodiment, the center sleeve 114 (of FIG. 7-8) may also provide feedback to the user through a variety of indicators, such as a light-emitting diode (LED) 100, a vibration 101, or an audible alert 102 when the user's movement is within or beyond a desired activity range. For example, if the user bends, twists, or moves at a rate that his physician has previously determined to exacerbate his back injury, the center sleeve 114 (of FIG. 7-8), or another associated piece of electronics, may emit a beeping noise, vibration, and/or flash a red LED to notify the user that his movements are out of range. While FIG. 9 illustrates one embodiment that includes the LED 100, the vibration 101, and the audible alert 102, alternative forms of audio and visual alerts may be utilized and are still considered within the scope of the present invention.

Furthermore, the center sleeve 114 of FIG. 9 may also include a power source 121 to provide power for the components of the device, as well as a clock 104, as previously discussed herein. The various devices of, or operably attached to, the center sleeve 114 can therefore communicate to the central computer 84 and user computers 88 via a wireless network device 82 to assist an investigator in analyzing movement, use, temperature, ultrasound, and electrical stimulation data. Although one embodiment of the center sleeve 114 is illustrated in FIG. 9, other arrangements of devices may be utilized according to what is deemed appropriate by one skilled in the art.

In this application, the terms "computer" or computer device may be a single personal computer platform in accordance to standard construction known to those skilled in the art, or any form of server, portable electronic device, tablet, cell phone, and/or any other electronic device known in the art. Furthermore, the terms "computer," "processor," "memory," and other computer related components, are hereby expressly defined to include any arrangement of one or more computer(s), processors, memory (chips or devices), and/or computer components, either as a single unit or operably connected and/or networked across multiple computers (or distributed computer components), to perform the functions described herein.

The precise quantification of physical activity is an important aim in both medical and fitness fields, as well as many related fields. The ability to accurately measure an individual's movement, or lack thereof, is critical when working with injured, sedentary, or frail populations because it allows clinicians to ascertain an individual's level of functioning and how to best intervene to improve his or her quality of life. The present belt-mounted movement sensor system 10 allows investigators to move beyond time-consuming direct observation and inaccurate self-report questionnaires in order to collect data in both an objective and practical manner.

The system 10 also enables many novel methods regarding non-medical fields. For example, the system 10 may be used to monitor employees for purposes of tracking methods of accomplishing tasks, to maximize productivity and avoid injuries. The system also enables tracking of productivity, and monitoring of injured employees (e.g., to prevent fraud). While several embodiments are mentioned herein, the scope of the present invention further includes alternative embodiments that could be devised by one skilled in the art given the teachings of the present invention.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A belt-mounted movement sensor system for tracking and recording movement data of a midsection of a user, the system comprising:
    a flexible belt shaped to be worn around and abut the midsection of the user;
    an array of accelerometers disposed on or within the flexible belt to physically associate with positions on the midsection of the user, each of the array of accelerometers having a sample rate that can be configured for sensing body movement during a movement activity;
    a power source operably connected to the array of accelerometers;
    a data collection system operably connected to the array of accelerometers, the data collection system having a means for receiving data from the array of accelerometers and processing that data into a storable format;
    wherein the array of accelerometers includes at least two central accelerometers that are mounted in a line on the flexible belt in a manner that allows them to align with the spine of the user when the flexible belt is worn;
    wherein the array of accelerometers further includes at least one left-side accelerometer;
    a means for adjustably mounting the left-side accelerometer on the flexible belt such that the left-side accelerometer is operably positioned on the left side of the user when the at least two central accelerometers are aligned with the spine of the user;
    wherein the array of accelerometers further includes at least one right-side accelerometer; and
    a means for adjustably mounting the right-side accelerometer on the flexible belt such that the right-side accelerometer is operably positioned on the right side of the user when the at least two central accelerometers are aligned with the spine of the user.

2. A belt-mounted movement sensor system for tracking and recording movement data of a midsection of a user, the system comprising:
    a flexible belt shaped to be worn around and abut the midsection of the user, the flexible belt having an outer shell constructed of a flexible fabric that includes an inner portion is shaped to abut the user, and an outer portion that covers the inner portion;
    an array of accelerometers disposed on or within the flexible belt to physically associate with positions on the midsection of the user, each of the array of accelerometers having a sample rate that can be configured for sensing body movement during a movement activity;
    a power source operably connected to the array of accelerometers;
    a data collection system operably connected to the array of accelerometers for receiving data from the array of accelerometers and processing that data into a storable format;
    wherein the array of accelerometers includes a central accelerometer that is mounted on the flexible belt in a manner that allows it to be positioned over the spine of the user when the flexible belt is worn; and
    further comprising heating coils, positioned between the inner portion and the outer portion of the outer shell, abutting the inner portion of the outer shell so that the inner portion adjacent the heating coils abuts the user on either side of the central accelerometer, so that heat from the heating coils is transferred by conduction to the user's back on both sides of the user's spine.

* * * * *